(12) United States Patent
Bhide et al.

(10) Patent No.: US 10,556,069 B2
(45) Date of Patent: Feb. 11, 2020

(54) INHALER

(71) Applicant: LUPIN LIMITED, Mumbai (IN)

(72) Inventors: Vishwajit Bhide, Mumbai (IN); Raghuram Amperayani Pattabhi, Baltimore, MD (US); Rohini Pimple, Maharashtra (IN); Bishu Choubey, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 649 days.

(21) Appl. No.: 15/121,430

(22) PCT Filed: Feb. 23, 2015

(86) PCT No.: PCT/IB2015/051350
§ 371 (c)(1),
(2) Date: Aug. 25, 2016

(87) PCT Pub. No.: WO2015/128789
PCT Pub. Date: Sep. 3, 2015

(65) Prior Publication Data
US 2016/0375207 A1    Dec. 29, 2016

(30) Foreign Application Priority Data

Feb. 25, 2014  (IN) .......................... 633/MUM/2014

(51) Int. Cl.
*A61M 15/00*    (2006.01)

(52) U.S. Cl.
CPC ...... *A61M 15/0026* (2014.02); *A61M 15/003* (2014.02); *A61M 15/0041* (2014.02);
(Continued)

(58) Field of Classification Search
CPC ............ A61M 11/003; A61M 15/0021; A61M 15/0025; A61M 15/0026; A61M 15/0028;
(Continued)

(56) References Cited

U.S. PATENT DOCUMENTS 3,807,400 A    4/1974  Cocozza
7,252,087 B2   8/2007  Wachtel
(Continued)

FOREIGN PATENT DOCUMENTS

WO    2012/047182 A2    4/2012

OTHER PUBLICATIONS

International Search Report and Written Opinion from International Patent Application No. PCT/IB2015/051350, dated May 20, 2015.
(Continued)

*Primary Examiner* — Annette Dixon
(74) *Attorney, Agent, or Firm* — Merchant & Gould P.C.

(57) ABSTRACT

An inhaler device comprising: a housing (2), a base plate (4) covering the housing (2), a medicament holder (10) integrated with the base plate (4), a mouthpiece (3) sitting over the base plate (4), a lid (1) which covers the mouthpiece (3), at least one piercing element (11), an actuating member (5), a spring (12), and is characterized in that the inhaler device is a two hinges system (6,8) wherein the base plate (4) is joined to hinge (6); the mouthpiece (3) and the lid (1) are joined to the hinge (8).

10 Claims, 8 Drawing Sheets

(52) U.S. Cl.
CPC ..... *A61M 15/002* (2014.02); *A61M 2202/064* (2013.01); *A61M 2205/586* (2013.01)

(58) Field of Classification Search
CPC ............ A61M 15/003; A61M 15/0033; A61M 15/0035; A61M 15/0036; A61M 15/0041; A61M 15/0043; A61M 15/0045; A61M 15/0048; A61M 15/0081; A61M 15/0086; A61M 2202/064; A61M 2205/276; A61M 2205/6045; A61M 2205/75; A61M 2206/16

See application file for complete search history.

(56) References Cited

U.S. PATENT DOCUMENTS

| 7,284,553 | B2 | 10/2007 | Hochrainer |
| 7,694,676 | B2 | 4/2010 | Wachtel |
| 8,006,695 | B2 | 8/2011 | Lulla et al. |
| 8,022,082 | B2 | 9/2011 | Zierenberg |
| 2006/0237016 | A1 | 10/2006 | Wachtel |
| 2010/0083962 | A1* | 4/2010 | Von Schuckmann ........................ A61M 15/0045 128/203.15 |
| 2013/0047985 | A1* | 2/2013 | Harris ............... A61M 15/0028 128/203.15 |
| 2014/0318538 | A1* | 10/2014 | Bilgic ............... A61M 15/0028 128/203.15 |
| 2016/0279355 | A1* | 9/2016 | Malhotra ............ A61M 15/003 |

OTHER PUBLICATIONS

Benjamin P. Best, "Nuclear DNA Damage as a Direct Cause of Aging," Rejuvenation Research, vol. 12, No. 3, pp. 199-208 (2009).

Dubaele et al., "Basal Transcription Defect Discriminates between Xeroderma Pigmentosum and Trichothiodystrophy in XPD Patients," Molecular Cell, vol. 11, pp. 1635-1646 (Jun. 2003).

Bernstein et al., "DNA repair/pro-apoptotic dual-role proteins in five major DNA repair pathways: fail-safe protection against carcinogenesis," Mutat Res., 511(2), pp. 145-178 (Jun. 2002).

* cited by examiner

INHALER

CROSS-REFERENCE TO RELATED APPLICATIONS

This application is a National Stage Application of International Patent Application No. PCT/IB2015/051350, filed 23 Feb. 2015, which claims benefit of Serial No. 663/MUM/2014, filed 25 Feb. 2014 in India and which applications are incorporated herein by reference. To the extent appropriate, a claim of priority is made to each of the above disclosed applications.

FIELD OF THE INVENTION

The present invention relates to an inhalation device for inhalation of powdered pharmaceutical compositions contained in capsules which are inserted in a medicament holder of the inhalation device.

BACKGROUND OF THE INVENTION

The invent of inhalation devices paved a hassle free path for the treatment and management of respiratory disorders. Today dry powder inhalation devices play an important role in the field of targeted drug delivery to the affected airways of lungs. Dry powder inhalers (DPIs) have been available since 1967 and Aventis was first to develop DPI by name SPINHALER for the delivery of Sodium Cromoglycate. Since then, many improvements in the design and use of inhalation devices were observed.

In general the powdered inhalation devices are used for inhaling either single or multi-dose of powdered medicament from capsules. The devices are configured to have medicament holders which hold the capsules containing the powdered medicament. A piercing mechanism provided with the device pierces the capsule and enables the medicament to get dispersed into the air sucked by the user during the process of inhalation. The emptied capsule remains in the device which is then discarded prior to the next use of the device.

U.S. Pat. No. 3,807,400 discloses some improvements in the inhaling devices with whirling chamber, devices that may be considered in their essential operation per se known and are intended to disperse the contents of a capsule filled with a powder medicinal composition. The device according to the invention provides a mouth piece that is a telescopic structure and two piercing devices that are placed into a rotatable member according to a diametral opposed position and are actuated by the member, the telescoping structure when extended forming the whirling chamber, the mantel of the latter mentioned member being formed with a cam able to give a number of piercing operations to both piercing devices.

U.S. Pat. No. 8,006,695 describes an inhaler device for inhalation of a medicament from a pierceable capsule comprises a housing for receiving a medicament capsule; closure means for closing the housing, said closure means being moveable relative to the housing; piercing means suitable for piercing a medicament capsule; wherein movement of the closure means relative to the housing causes movement of the piercing means. The invention also provides a holder for a medicament capsule which holder comprises a chamber suitable for receiving a medicament capsule; and means for generating turbulence in a fluid flow through the chamber such that, in use, the turbulent fluid flow causes vibration of a capsule received by the chamber so as to assist in releasing medicament contained within the capsule.

U.S. Pat. No. 7,694,676 describes an inhaler for inhaling powdered pharmaceutical compositions from capsules includes: a lower part; a plate which can be latched to the lower part and with which the lower part can be closed off; a capsule holder for receiving the capsules, this holder being adapted to be lowered into the lower part; a mouthpiece latchable to the plate; a lid which covers the mouthpiece in a closed position and latches it by means of a closure element, the lower part, the plate, the mouthpiece and the lid being hinged together by means of a single joint.

U.S. Pat. No. 8,022,082 discloses an inhaler comprising: a housing containing two windows, a deck in which there are air inlet ports and which is provided with a screen secured by a screen housing, an inhalation chamber connected to the deck on which there is a push button provided with two sharpened pins and movable counter to a spring, a mouthpiece which is connected to the housing, the deck, and a cover via a spindle to enable it to be flipped open or shut, and three holes with diameters below 1 mm in the central region around the capsule chamber and underneath the screen housing and screen.

U.S. Pat. No. 7,252,087 discloses an inhaler utilizing a multi-functional actuating member. Multi-functional actuating member as disclosed in US '087 in a first functional position allows a closure element to be disengaged from a lower part of the housing, and in a second functional position allows a mouthpiece to be pivoted away from the lower part of the housing.

U.S. Pat. No. 7,284,553 discloses a powder inhaler operating on the Bernoulli principle. It discloses an inhaler with a capsule chamber including raised elements on either the inner surface of the capsule chamber or on the outer surface of the capsule.

Although the prior art discussed many different kinds of inhalers for the delivery of medicament, a need still remains in the art for design and development of improved inhalers for powdered inhalant delivery based on the factors that influence treatment compliance such as drug to be delivered, ease of handling and patient's preference. The present invention therefore aims at adequately addressing these and other needs existing in the art by improving the known inhalers further in terms of their handling.

The invention is thus concerned with improved inhaling devices with two hinge system intended to disperse the contents of the powdered pharmaceutical composition.

In the normal use of the Dry Powder Inhaler; patient opens the lid, then the mouth piece and inserts the capsule containing powdered pharmaceutical composition. Patient then presses the actuating member that leads to piercing of the capsule containing powdered pharmaceutical composition. The piercing elements attached to the actuating member pierce the capsule from one side allowing the powdered pharmaceutical composition contained in the capsule to come out when the patient inhales from the mouthpiece.

The 'two hinge' design in the inhaler of present invention employs two separate hinges. One hinge is for the lid and the mouth piece and second is for the base plate. The patient is required to open the base plate only as and when required. Use of second and distinct hinge prevents the accidental opening of the base plate, thereby avoiding the contamination of the medicament. Also, the non-protruding actuating member makes handling and storing of the device very convenient.

Further, the shape of the inhaler which is round across the top and on one side is configured at an angle in such a way that patient is able to have an appropriate grip on the device and finds it very convenient to actuate the device without losing control over the holding of the device

OBJECTS OF INVENTION

An object of the present invention is to overcome the drawbacks of the prior art.

Another object of the present invention is to provide an inhaler device with two hinge systems (6, 8).

Yet another object of the present invention is to provide an inhaler device with two hinge systems, wherein the mouthpiece (3) and the lid (1) is joined to a single hinge (8).

Yet another object of the present invention is to provide an inhaler device with two hinge systems, wherein the base plate (4) is hinged separately from the mouthpiece and lid to hinge (6).

Yet another object of the present invention is to provide an inhaler utilizing base plate (4) devoid of any holes.

Yet another object of the present invention is to provide an inhaler wherein the gripping aid (9) is disposed distal to the actuating member (5).

SUMMARY OF THE INVENTION

Accordingly to one aspect of the present invention there is provided an inhaler device comprising: a housing (2), a base plate (4) covering the housing (2), a medicament holder (10) integrated with the base plate (4), a mouthpiece (3) sitting over the base plate (4), a lid (1) which covers the mouthpiece (3), at least one piercing element (11), an actuating member (5), a spring (12), and is characterized in that the inhaler device is a two hinge system (6,8) wherein the base plate (4) is joined to hinge (6); the mouthpiece (3) and the lid (1) are joined to the hinge (8).

BRIEF DESCRIPTION OF THE ACCOMPANYING DRAWINGS

FIG. 1 illustrates the essential components of the inhaler in accordance with the present invention wherein the housing (2) which accommodates the base plate (4) and is covered by the latter, the mouthpiece (3) with gripping aid (9). The base plate (4) is joined to the hinge (6) and the mouthpiece (3) and the lid (1) is hinged together distinctly from the base plate to hinge (8). The gripping aid (9) is disposed distal to the actuating member (5).

DETAILED DESCRIPTION OF THE INVENTION

Figure 1:
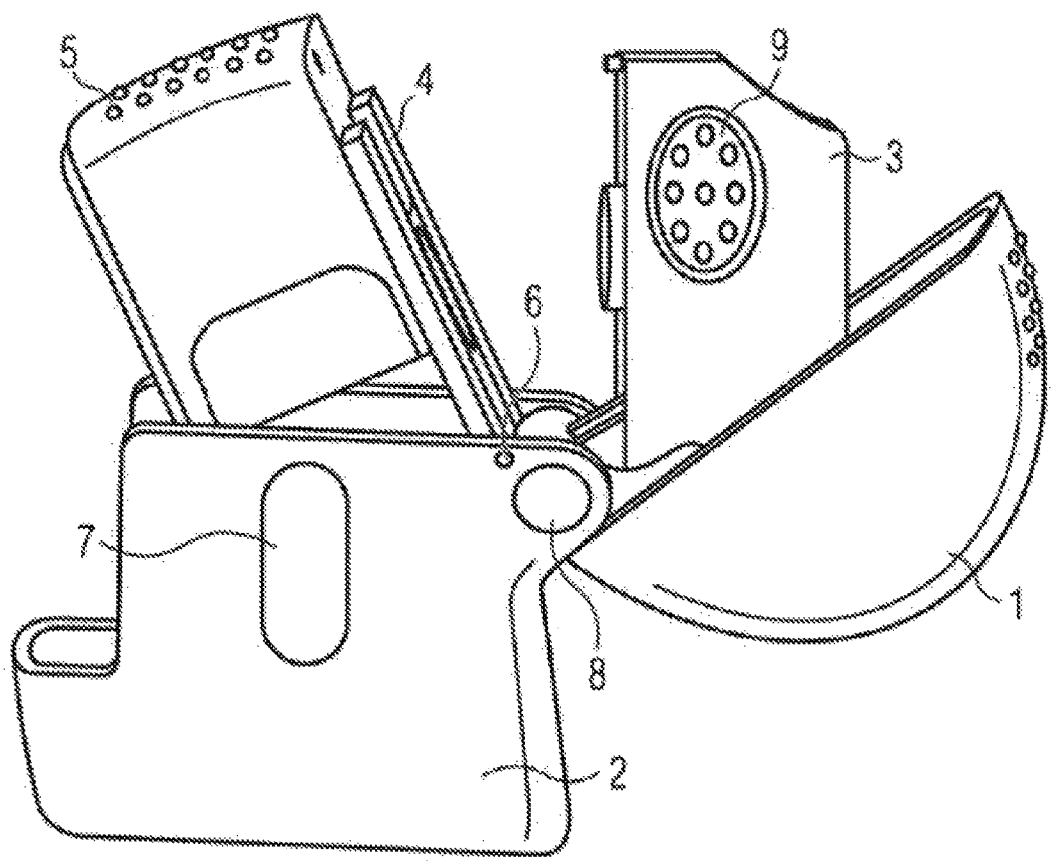
Figure 2:
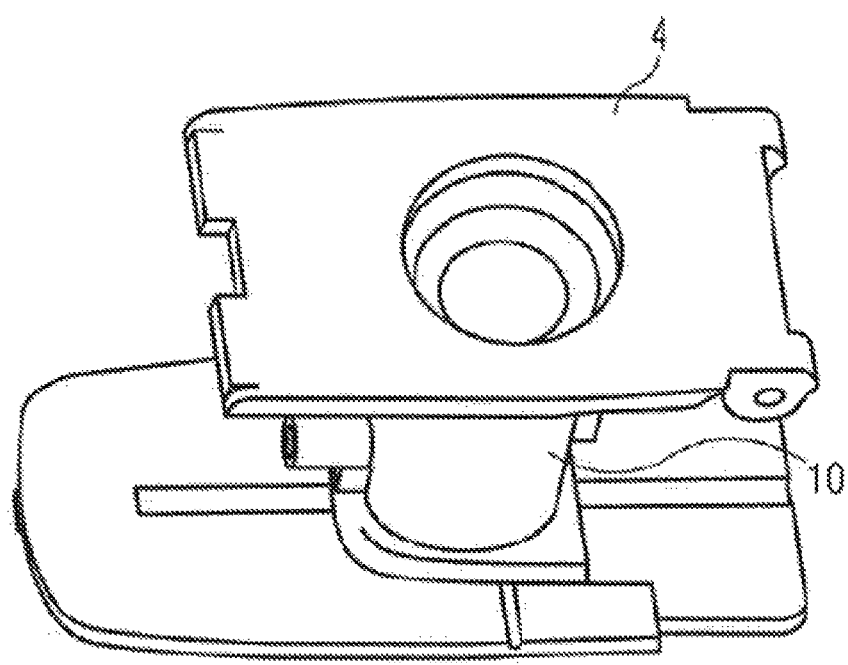
FIG. 2 illustrates the Top view of the medicament holder (10) mounted on the underside of the base plate (4).
Figure 3:
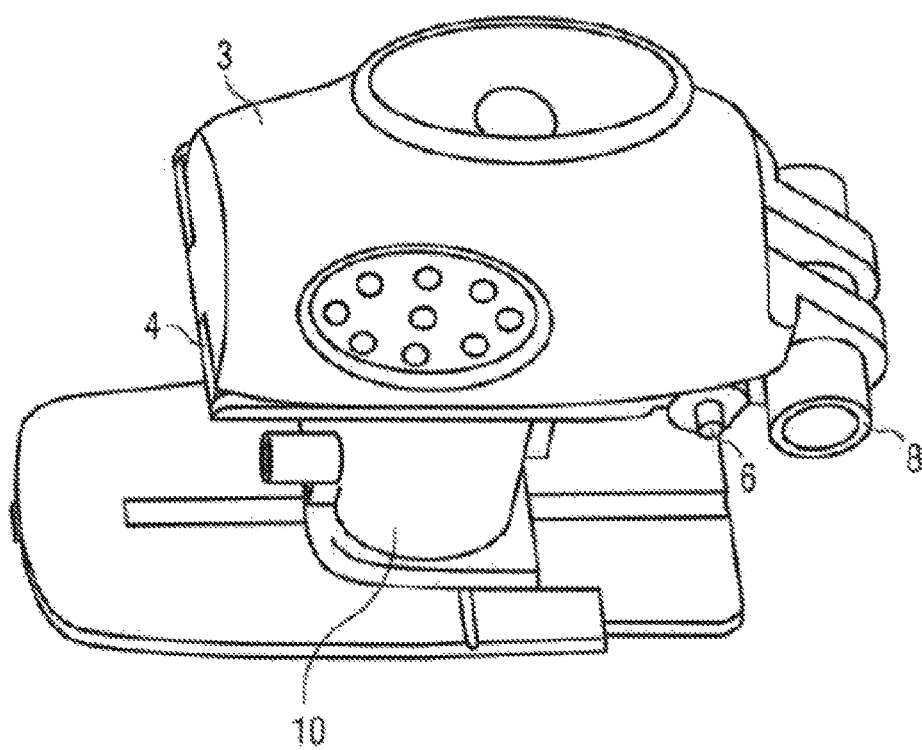
FIG. 3 illustrates the closed view of the mouthpiece (3) sitting over the base plate (4) that is integrated with the medicament holder (10). The two hinges (6, 8) are distinctly marked.
Figure 4:
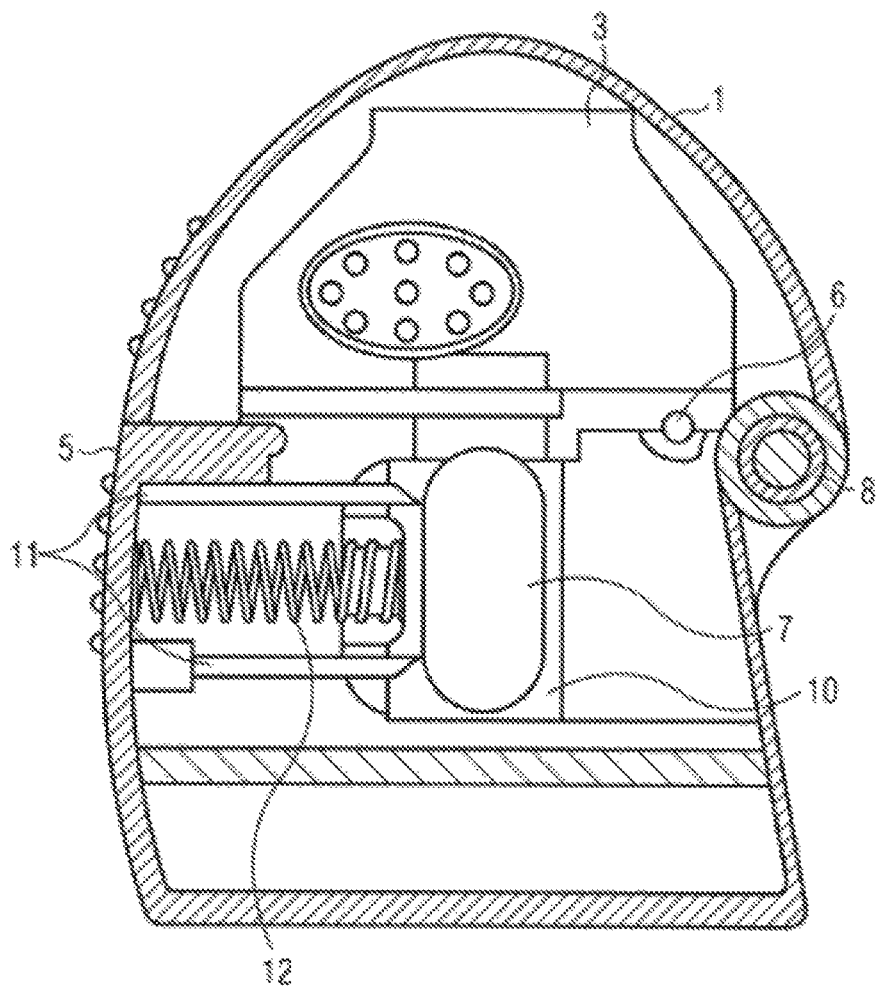
FIG. 4 illustrates the radial partial sectional view of the inhaler depicting the lid (1), mouthpiece (3), piercing elements (11), actuating member (5), spring (12), medicament holder (10), inspection windows (7), and the mouthpiece and lid attached to hinge (8).
Figure 5:
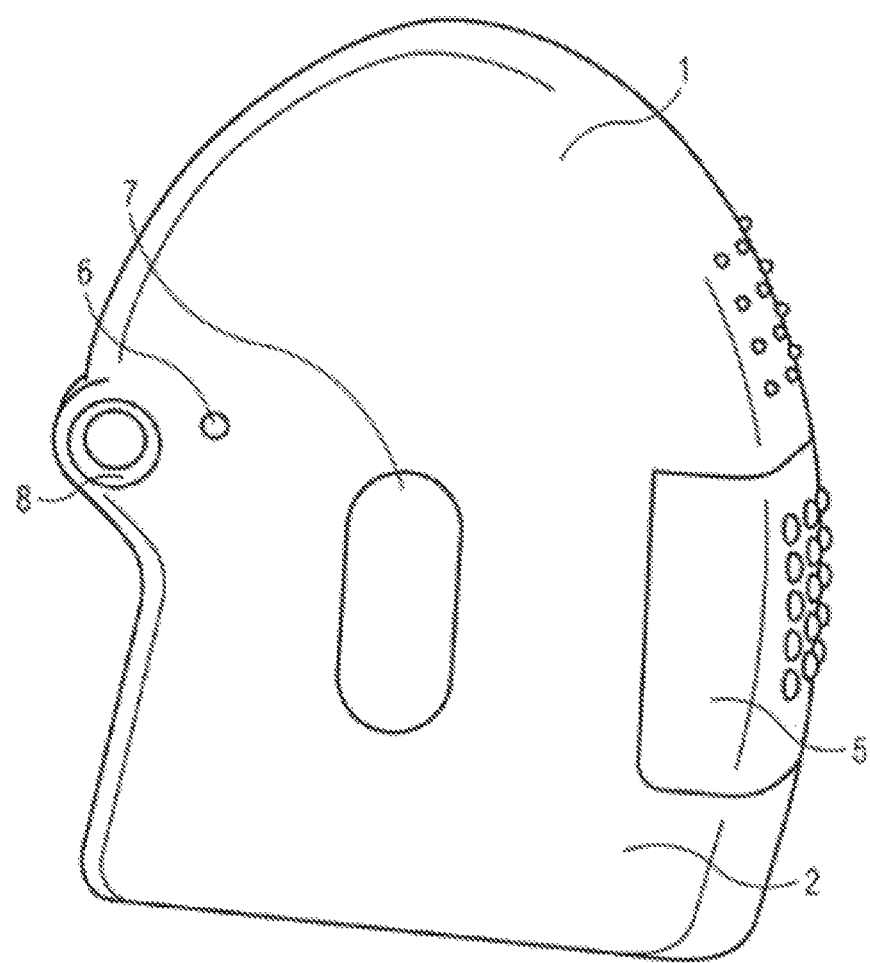
FIG. 5 illustrates the side perspective of the inhaler in a fully closed position.
Figure 6:
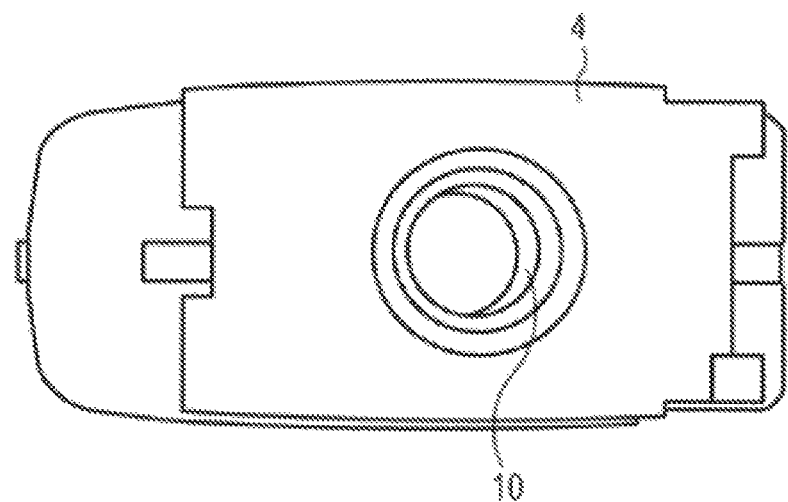
FIG. 6 illustrates the top view of the inhaler base plate (4) devoid of any holes.
Figure 7:
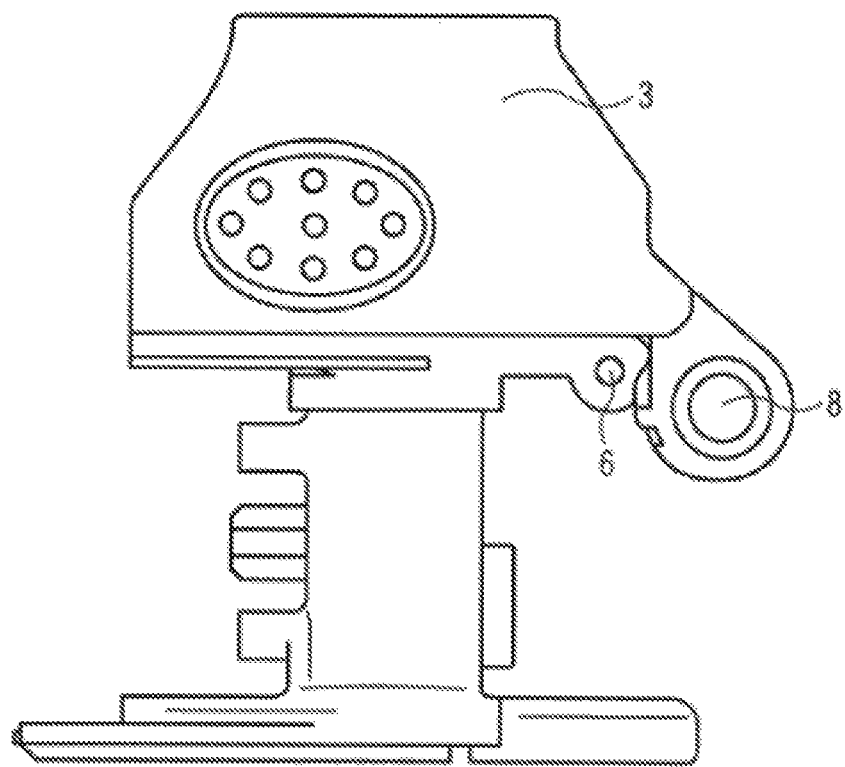
FIG. 7 illustrates the inhaler with distinct two hinge system (6, 8).

The following presents a simplified summary of the invention in order to provide a basic understanding of some aspects of the invention. This summary is not an extensive overview of the present invention. It is not intended to identify the key/critical elements of the invention or to delineate the scope of the invention. Its sole purpose is to present some concept of the invention in a simplified form as a prelude to a more detailed description of the invention presented later.

In accordance with present invention an inhaler for inhaling powdered pharmaceutical compositions is provided from capsules which are inserted in a medication holder provided in the inhaler before use. According to the present invention, after the capsule has been inserted in the medication holder of the device, the patient can press an actuating member which can be moved from a resting position, thereby cooperating with at least one piercing element which can enter into the medication holder. The capsule is pierced by the minimum of one piercing element and the pharmaceutical composition is released.

Other aspects, advantages, and salient features of the invention will become apparent to those skilled in the art from the following detailed description, which, taken in conjunction with the annexed drawings, discloses exemplary embodiments of the invention.

The inhaler according to the present invention as shown in the FIGS. 1, 2, 3 and 4 essentially comprises of a housing (2) which accommodates the base plate (4) and is covered by the latter, the mouthpiece (3) with gripping aid (9); the said base plate (4) is joined to the hinge (6) and the mouthpiece (3) and the lid (1) is hinged together distinctly from the base plate to hinge (8); The gripping aid (9) is disposed distal to the actuating member (5). Inspectional window (7) further allows to inspect the internal elements of the device. A medicament holder (10) is mounted on the underside of the base plate (4). One or more piercing elements (11) for piercing the capsules are attached from inside of the actuating member (5) and a spring (12) is also configured to link the actuating member; characterized in that the actuator when pressed from outside, the spring (12) gets compressed and enables the piercing elements (11) to move linearly and pierce the capsule such that the medicament inside the capsule is released and the spring retracts thereafter.

The terms and words used in the following description and claims are not limited to the bibliographical meanings, but, are merely used by the inventor to enable a clear and consistent understanding of the invention.

Lid (1) offers protection to the device components by preventing entry of dust or any other extraneous particles.

Mouthpiece (3) is the component through which the patient inhales the powdered pharmaceutical composition.

Base plate (4) ensures that the medicament holder (10) is held securely and always remains aligned to the mouthpiece (3) for a smooth flow of the medicament.

Actuating member (5) is responsible for locking & unlocking of the lid (1) and holds the piercing elements (11) in an appropriate position. When the actuating member (5) is moved forward, it ensures appropriate piercing of the capsule in such a way that the powdered pharmaceutical composition is available for inhalation by the patient.

Hinge (6) is responsible for holding the base plate (4) in an appropriate position in such a way that the medicament holder (10) is always aligned to the mouthpiece (3).

Inspection window (7) provides a view of the medicament holder (10) and allows the patient to confirm the presence of capsule in the medicament holder (10).

Hinge (8) is responsible for appropriate movement of the lid (1) and mouthpiece (3).

Gripping aid (9) on the mouthpiece offers a grip for the patient to open the mouthpiece so that the capsule containing the powdered pharmaceutical composition could be placed in the medicament holder (10).

In an embodiment of present invention, the inhaler is operated in the following manner
- a) The lid (1) is opened by pressing the actuating member (5)
- b) The lid (1) is pulled upwards and away from the base to expose the mouthpiece (3)
- c) The mouthpiece (3) is opened by pulling the gripping aid (9) located on both sides of the mouthpiece (3).
- d) The capsule is placed in the medicament holder (10) of the inhaler of the present invention
- e) The mouthpiece (3) is closed firmly. The lid (1) is kept open.
- f) The inhaler of the present invention is held in such a position that the mouthpiece (3) is pointed upwards
- g) The actuating member (5) is pressed to move the piercing element (11) to pierce the capsules.
- h) The powdered pharmaceutical composition is inhaled from the capsule.

The device may be made from any suitable material. Preferably the device is made of plastic, for example ABS (acrylonitrile butadiene styrene), PC (polycarbonate), PA (polyacetal) or PS (polystyrene), or mixtures thereof, or of an antistatic material such as delrin or stainless steel The inhaler according to the invention allows the pharmaceutical composition to be delivered more reliably compared to the devices known from the prior art.

The advantages of the present inhaler are as follows.
1. The patient is required to open the base plate only as and when required. Use of second and distinct hinge prevents the accidental opening of the base plate, thereby avoiding the contamination of the medicament.
2. Also, the non-protruding actuating member makes handling of the device and storing of the device, very convenient.
3. Further, the shape of the inhaler which is round across the top and on one side, is configured at an angle in such a way that patient is able to have an appropriate grip on the device and finds it very convenient to actuate the device without losing control over the holding of the device An inhaler device with two hinge system utilizing a base plate devoid of any holes was measured to have a flow resistance of about 0.07/L min$^{-1}$, resulting in a flow rate of about 40 L min$^{-1}$ with a pressure drop of about 4 kPa across the inhaler.

The flow resistance can be calculated using the formulae:

$$R = P^{0.5}/Q$$

where Q is the flow rate (L/min), P is the pressure drop (kPa) across the inhaler and R is the flow resistance [kPa$^{0.5}$/(L/min)].

In the system, the inhalation pressure drops of between 2 kpa and 6 kpa produced resultant flow rates of about between 25 and 55 liters per minute.

The present invention relates to the use of an inhaler device as described above for the administration of powdered pharmaceutical composition that is suitable for the treatment of asthma or chronic obstructive pulmonary disease by inhalation.

The pressure drop versus flow rate curve depends upon the construction of the inhaler.

The inhaler in accordance with the present invention was tested to measure its resistance to flow which is an important characteristic of inhalers.

Figure 8:
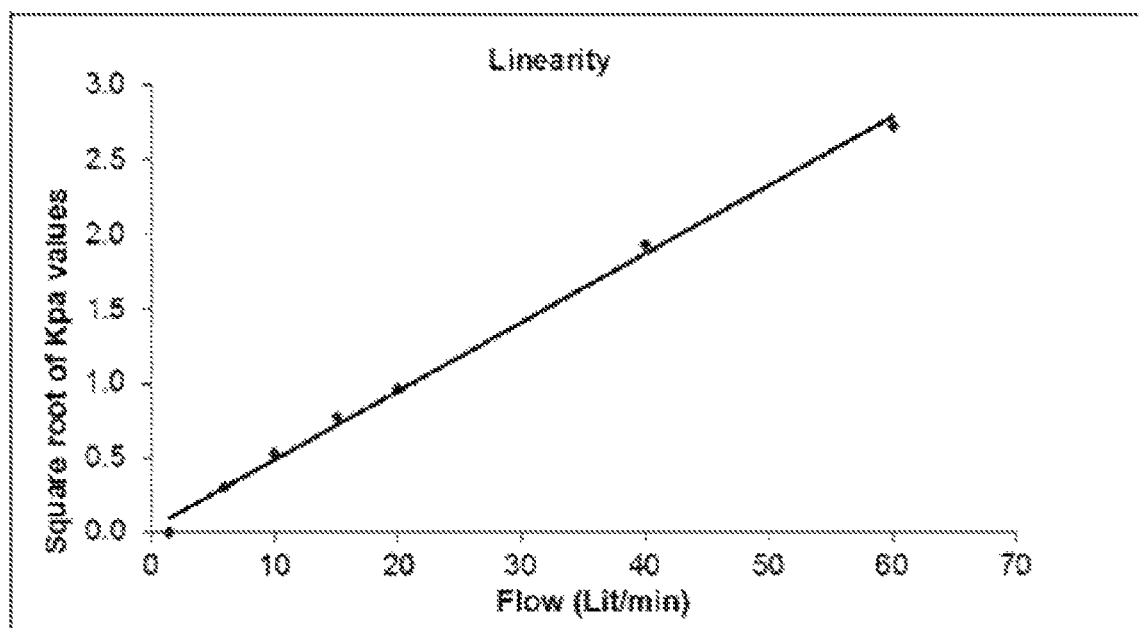
FIG. 8 illustrates the graph for square root of the pressure drop versus the flow rate in the present inhaler depicting relatively high resistance to air flow.

According to the Bernoulli principle, when the square root of the pressure drop is plotted versus the flow rate, the resistance of the inhaler is the slope of the linear portion of the curve. An exemplary graph can be seen in FIG. 8 for an inhaler device in accordance with the present invention. The graph depicted in FIG. 8 indicates relatively high resistance to air flow, the curve increasing rapidly with the flow rate.

The inhaler according to the present invention may include design features provided by the recognition that different powdered drugs have different characteristics. Thus, for increased delivery efficiency, the flow parameters of the inhaler should advantageously be adjusted for the specific drug being delivered. These adjustments can be made by adjusting the air flow. The air flow can be controlled by drilling additional air supply hole or by increasing and decreasing the size of the opening of the air supply hole.

Preferably, the powdered pharmaceutical composition contained within the capsule is a dry powder medicament. The term capsule is intended to be understood broadly and includes any suitable receptacle for powdered pharmaceutical compositions. The capsule may be formed from any suitable material, including gelatin, HPMC, or plastic.

In an embodiment the invention provides pharmaceutical composition which includes powdered pharmaceuticals can be administered by inhalation. Particularly preferred in this context are pharmaceutical compositions selected from among the anticholinergics, beta-2-agonists, steroids, PDE IV-inhibitors, LTD4-antagonists and EGFR-kinase inhibitors.

Anticholinergics for use are preferably selected from among TIOTROPIUM bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, 2,2-diphenylpropionate cyclopropyltropine methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl 4,4'-difluorobenzilate cyclopropyltropine methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Beta-2-agonists used are preferably selected from among albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamin-o]ethanol, 1-[3-(4-methoxybenzyl-amino)-4-hydroxyphenyl]-2-[4-(1-benzimida-zolyl)-2-methyl-2-butylamino]ethanol, 1-[2H-5-hydroxy-3-oxo-4H-1,4-benzoxazin-8-yl]-2-[3-(4-N,N-dimethylaminoph-enyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1-,2,4-triazol-3-yl]-2-methyl-2-butylamino}ethanol, 5-hydroxy-8-(1-hydroxy-2-isopropylaminobutyl)-2H-1,4-benzoxazin-3-(4H)-on-e, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)-ethanol, optionally in the form of the racemates, enantiomers or diastereomers thereof and optionally in the form of ihrer pharmacologically acceptable acid addition salts, solvates and/or hydrates thereof.

The steroids used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl6.quadrature., 9.quadrature.-difluoro-17.quadrature.-[(2-f-uranylcarbonyl)oxy]-11.quadrature.-hydroxy-16.quadrature.-methyl-3-oxo-and-rosta-1,4-diene-17.quadrature.-carbothionate, (S)-(2-oxo-tetrahydro-furan-3S-yl) 6.quadrature., 9.quadrature.-difluoro-11.quadrature.-hydroxy-16.quadrature-.-methyl-3-oxo-17.quadrature.-propionyloxy-androsta-1,4-diene-17.quadratur-e.-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV inhibitors used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethox-ybenzamide, NCS-613, pumafentine, (−)p-[(4aR*,10bS*)-9-ethoxy-1,2,3,4,4a,10b-hexahydro-8-methoxy-2-methylbe-nzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrol-idone, 3-(cyclopentyloxy-4-methoxyphenyl)-1-(4-N'—[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyph-enyl)cyclohexan-1-one, cis[4-cyano-4-(3-cyclopropylmethoxy-4-difluoromethoxyphenyl)cyclo-hexan-1-ol], (R)-(+)-ethyl[4-(3-cyclopentyloxy-4-methoxyphenyl)pyrrolidin-2-yliden-e]acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, CI-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers thereof and optionally in the form of the pharmacologically acceptable acid addition salts thereof, solvates and/or hydrates thereof.

LTD4-antagonists used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phen-yl)-3-(2-(1-hydroxy-1-methylethyl)phenyl)propyl)thio)methyl)cyclopropanace-tic acid, pranlukast, zafirlukast, [2-[[2-(4-tert-butyl-2-thiazolyl)-5-benzofuranyl]oxymethyl]phenyl] acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof as well as optionally in the form of the salts and derivatives thereof, the solvates and/or hydrates thereof. EGFR-kinase inhibitors used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]-amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoli-ne, 4-[(3-chloro-4-fluorophenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-am-ino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-am-ino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-am-ino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-bute-n-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino-)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-o-xo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7- methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cycl-ohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piper-idin-4-yloxy}-7-methoxy-quinazoline, 4-[(3-chloro-4-fluoro-phenyl)amino]-6-(piperidin-3-yloxy)-7-methoxy-quina-zoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonyla-mino]-cyclohexan-1-yloxy}-7-methoxy-quinazoline, 4-[(3-chloro-4-fluoro-phenyl)amino]-6-{1-[(piperidin-1-yl)carbonyl]-piper-idin-4-yloxy}-7-methoxy-quinazoline, 4-[(3-chloro-4-fluoro-phenyl)amino]-6-(cis-4-{N-[(morpholin-4-yl)carbony-1]-N-methyl-amino}-cyclohexan-1-yloxy)-7-methoxy-quinazoline, 4-[(3-chloro-4-fluoro-phenyl)amino]-6-(trans-4-ethansulphonylamino-cycloh-exan-1-yloxy)-7-methoxy-quinazoline, 4-[(3-chloro-4-fluoro-phenyl)amino]-6-(1-methanesulphonyl-piperidin-4-ylo-xy)-7-(2-methoxy-ethoxy)-quinazoline, 4-[(3-chloro-4-fluoro-phenyl)amino]-6-[1-(2-methoxy-acetyl)-piperidin-4-y-loxy]-7-(2-methoxy-ethoxy)-quinazoline, 4-[(3-ethynyl-phenyl)amino]-6-(tetrahydropyran-4-yloxy]-7-methoxy-quinazo-line, 4-[(3-chloro-4-fluorophenyl)amino]-6-(cis-4-{N-[(piperidin-1-yl)car-bonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylami-no]-cyclohexan-1-yloxy}-7-methoxy-quinazoline, 4-[(3-chloro-4-fluorophenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-meth-oxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-me-thoxy-ethoxy)-quinazoline, 4-[(3-ethynyl-phenyl)amino]-6-{1-[(morpholin-4-yl)carbonyl]-piperidin-4-y-loxy}-7-methoxy-quinazoline, 4-[(3-chloro-4-fluorophenyl)amino]-6-{1-[(N-methyl-N-2-methoxyethyl-amin-o)carbonyl]-piperidin-4-yloxy}-7-methoxy-quinazoline, 4-[(3-chloro-4-fluoro-phenyl)amino]-6-(1-ethyl-piperidin-4-yloxy)-7-metho-xy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cy-clohexan-1-yloxy)-7-methoxy-quinazoline, 4-[(3-chloro-4-fluoro-phenyl)amino]-6-(trans-4-methyl-amino-cyclohexan-1-y-loxy)-7-methoxy-quinazoline, 4-[(3-chloro-4-fluoro-phenyl)amino]-6-[trans-4-(N-methanesul-phonyl-N-meth-yl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluorophenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-ylo-xy)-7-methoxy-quinazoline, 4-[(3-chloro-4-fluoro-phenyl)amino]-6-(1-cyano-piperidin-4-yloxy)-7-metho-xy-quinazoline, and 4-[(3-chloro-4-fluoro-phenyl)amino]-6-{1-[(2-methoxy-ethyl)carbonyl]-piper-idin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

Examples of acid addition salts with pharmacologically acceptable acids which the compounds may be capable of forming include salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

The powdered pharmaceutical compositions may contain the above-mentioned active substances as well as the salts, esters thereof, or combinations of these active substances, salts and esters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:
1. An inhaler device comprising:
a housing,
a base plate covering the housing,
a medicament holder integrated with the base plate,
a mouthpiece sitting over the base plate,
a lid which covers the mouthpiece,
at least one piercing element,
an actuating member,
a spring,
characterized in that a piercing element is attached from inside of the actuating member, the spring is configured to link the actuating member to the medicament holder and the inhaler device is a two hinge system, wherein
  the base plate is joined to a first hinge extending through a corresponding first set of apertures in said housing;
  the mouthpiece and the lid are joined to a second hinge extending through a corresponding second set of apertures in said housing, wherein the base plate is hinged separately from the mouthpiece and lid.
2. The inhaler device according to claim 1, wherein in order to assist piercing, the actuating member when pressed causes the spring element to get compressed which enables the piercing elements to move linearly.
3. The inhaler device according to claim 1, wherein the device further comprises a gripping aid on the mouthpiece which offers a grip to open the mouthpiece.
4. The inhaler device according to claim 3, wherein the gripping aid is disposed distal to the actuating member.
5. The inhaler device according to claim 1, wherein the device further comprises an inspection window to see across the inhaler device.
6. The inhaler device according to claim 1, wherein the medicament holder is mounted on the underside of the base plate.
7. The inhaler device according to claim 1, wherein the base plate is devoid of any holes.

8. The inhaler device according to claim 1, wherein the medicament holder is designed to contain a capsule with powdered pharmaceutical composition.

9. The inhaler device according to claim 8, wherein the powdered pharmaceutical composition is suitable for the treatment of asthma or chronic obstructive pulmonary disease by inhalation.

10. The inhaler device according to claim 8, wherein the powdered pharmaceutical composition contained within the capsule is a dry powder medicament.

* * * * *